US011110431B2

(12) United States Patent
Nedez et al.

(10) Patent No.: US 11,110,431 B2
(45) Date of Patent: Sep. 7, 2021

(54) ALUMINA HAVING ACIDITY AND STRUCTURE WITH A POROSITY WHICH ARE OPTIMAL

(71) Applicant: AXENS, Rueil Malmaison (FR)

(72) Inventors: Christophe Nedez, Rueil Malmaison (FR); Olivier Ducreux, Rueil Malmaison (FR)

(73) Assignee: AXENS, Rueil Malmaison (FR)

( * ) Notice: Subject to any disclaimer, the term of this patent is extended or adjusted under 35 U.S.C. 154(b) by 19 days.

(21) Appl. No.: 16/521,813

(22) Filed: Jul. 25, 2019

(65) Prior Publication Data

US 2020/0030773 A1 Jan. 30, 2020

(30) Foreign Application Priority Data

Jul. 25, 2018 (FR) ...................................... 1856905

(51) Int. Cl.

| | |
|---|---|
| ***B01J 21/04*** | (2006.01) |
| ***B01J 35/10*** | (2006.01) |
| ***B01J 20/08*** | (2006.01) |
| ***B01J 20/28*** | (2006.01) |
| ***C07C 1/24*** | (2006.01) |

(52) U.S. Cl.

CPC ............... *B01J 21/04* (2013.01); *B01J 20/08* (2013.01); *B01J 20/28059* (2013.01); *B01J 20/28061* (2013.01); *B01J 20/28071* (2013.01); *B01J 20/28073* (2013.01); *B01J 35/1014* (2013.01); *B01J 35/1019* (2013.01); *B01J 35/1038* (2013.01); *B01J 35/1042* (2013.01); *B01J 35/1061* (2013.01); *B01J 35/1066* (2013.01); *C07C 1/24* (2013.01); *C07C 2521/04* (2013.01)

(58) Field of Classification Search

CPC ...... B01J 21/04; B01J 20/08; B01J 20/28059; B01J 20/28061; B01J 20/28073; B01J 35/1019; B01J 35/1038; B01J 35/1061; B01J 35/1066

See application file for complete search history.

(56) References Cited

U.S. PATENT DOCUMENTS

| | | | | |
|---|---|---|---|---|
| 5,324,878 | A * | 6/1994 | Brunelli | C07C 2/10 585/508 |
| 5,475,183 | A | 12/1995 | Araki et al. | |
| 6,790,422 | B1 | 9/2004 | Legendre et al. | |
| 7,125,538 | B2 * | 10/2006 | Le Loarer | B01J 20/08 423/625 |
| 8,022,261 | B2 * | 9/2011 | Kalyanaraman | C07C 2/66 585/467 |
| 8,785,707 | B2 * | 7/2014 | Cabiac | B01J 29/041 585/531 |
| 9,132,414 | B2 * | 9/2015 | Coupard | C07C 5/2775 |
| 9,902,662 | B2 | 2/2018 | Aribert et al. | |
| 2012/0245023 | A1 * | 9/2012 | Kressmann | B01J 21/04 502/322 |

FOREIGN PATENT DOCUMENTS

| | | | |
|---|---|---|---|
| EP | 0692306 | B1 | 1/2002 |
| EP | 3074368 | B1 | 12/2017 |
| JP | 2911244 | B2 | 6/1999 |

OTHER PUBLICATIONS

P Souza Santos: Materials Research vol. 3, No. 4, Oct. 1, 2000 pp. 104-114.

Search Report in corresponding FR1856905 dated Apr. 29, 2019 (pp. 1-2).

* cited by examiner

*Primary Examiner* — Melissa S Swain

(74) *Attorney, Agent, or Firm* — Millen, White, Zelano & Branigan, P.C.

(57) ABSTRACT

An alumina exhibiting a structure with a porosity such that the volume of the pores having a diameter of between 70 and 2000 Å is between 0.15 and 0.50 ml/g, and comprising at least one alkali metal (M), such that the content by weight of alkali metal, expressed as $M_2O$, is between 400 and 1500 ppm, with respect to the total weight of the alumina, and a process for the transformation of a feedstock comprising at least one alcohol into an olefinic effluent, said process comprising a stage of dehydration of said alcohol in the presence of the alumina according to the present invention, having an acidity and a structure with a porosity which are optimal.

16 Claims, No Drawings

ALUMINA HAVING ACIDITY AND STRUCTURE WITH A POROSITY WHICH ARE OPTIMAL

FIELD OF THE INVENTION

The invention relates to the field of the catalysis of the dehydration of alcohols to give olefins by an alumina having an acidity and a structure with a porosity which are optimal. It relates more particularly to an alumina exhibiting a reduced content of alkali metals and a structure with a porosity which is specific and to its use as catalyst, in particular of the reaction for the dehydration of alcohols, especially secondary and tertiary alcohols, or as adsorbent.

CONTEXT OF THE INVENTION AND STATE OF THE ART

Aluminas are used as catalysts of numerous chemical reactions and in particular of reactions requiring acidic operating conditions. This is the case, for example, with reactions for the dehydration of alcohols. In such reactions, the more active the alumina, the greater the conversion. There thus exists a need for aluminas exhibiting a high acidic nature.

Aluminas, in particular acidic aluminas, are also often used as absorbents.

However, an excessively acidic alumina can prove to be harmful as side reactions can occur, resulting in a lower yield for the desired reaction. In the reaction for the dehydration of alcohols, condensation and dehydrogenation reactions may take place. These interfering side reactions cause the yield to fall and may play a harmful role with regard to the stability of the alumina by reducing, in particular, its lifetime. For example, coke can be formed, blocking the porosity of the adsorbent and resulting in short lifetimes.

Numerous studies have been carried out in order to prepare aluminas which are optimized for the purpose of applications as catalyst, in particular of the reaction for the dehydration of alcohols, or as adsorbent.

Patent FR 2 780 392 describes an activated alumina with a content of alkali metals, expressed as $M_2O$, of between 500 and 8000 ppm by weight and a crystalline structure comprising at least 5% by weight of alumina of q phase. This alumina is used to catalyse the reactions for the dehydration of alcohols and for the isomerization of olefins, for which it exhibits satisfactory performance qualities within a range of high contents of alkali metals (greater than 2200 ppm by weight), the performance qualities being more restricted within the range of low contents of alkali metals (less than 1500 ppm by weight).

U.S. Pat. No. 9,145,342 describes a process for the production of isobutene by dehydration of tert-butyl alcohol in the gas phase, using an aluminous catalyst comprising a content of Na, expressed as $Na_2O$, of between 0.1% and 0.6% by weight (that is to say, between 1000 and 6000 ppm by weight) and a content of Si, expressed as $SiO_2$, of less than or equal to 0.4% by weight, and for which the structure with a porosity is such that the total pore volume is from 0.1 to 0.5 ml/g and the volume of the pores with a radius of greater than 70 Å is greater than 60% of the total pore volume. More particularly, the isobutene is produced with a satisfactory yield when the dehydration of the tert-butyl alcohol is carried out in the presence of an aluminous catalyst containing silica (at least 0.06% by weight of $SiO_2$), comprising at least 1300 ppm by weight of $Na_2O$ and exhibiting a volume of the pores with a radius of at least 70 Å corresponding to 74% and 78% of the total pore volume, itself in the vicinity of 0.2 ml/g.

In the field of adsorption, Patent EP 1 372 808 describes a process for the removal of the oxygen-comprising organic molecules, such as alcohols and organic acids, present in a liquid or gaseous organic effluent, by adsorption on alumina agglomerates which can comprise a doping compound, such as an alkali metal, at a content by weight, expressed as $M_2O$, of less than 5000 ppm, and which exhibit a structure with a porosity such that the volume of the pores having a diameter of greater than 70 Å is greater than or equal to 0.15 ml/g. This adsorbent captures the traces of alcohols and organic acids present in the stream to be treated by adsorbing them at ambient temperature.

The object of the present invention is to provide an alumina which can be used as catalyst of the reaction for the dehydration of alcohols, especially secondary and tertiary alcohols. In particular, the present invention provides an alumina which makes it possible to obtain good performances in the dehydration of alcohols, indeed even better performances than those of the aluminas known in the prior art.

SUMMARY OF THE INVENTION

The present invention relates to an alumina exhibiting a structure with a porosity such that the volume of the pores having a diameter of between 70 and 2000 Å is between 0.15 and 0.50 ml/g, and comprising at least one alkali metal (M), such that the content by weight of alkali metal, expressed as $M_2O$, is between 400 and 1500 ppm, with respect to the total weight of the alumina.

Surprisingly, the Applicant has discovered that the alumina according to the present invention, exhibiting a reduced content of alkali metals and a particular porous structure, in particular a specific volume of pores for the pores with a diameter of between 70 and 2000 Å which is between 0.15 and 0.50 ml/g, made it possible to obtain good performances in the dehydration of alcohols which are better than those of the aluminas known in the prior art. The Applicant has demonstrated that such an alumina makes it possible to obtain a very good conversion of the alcohols into olefins, a better selectivity and an improved stability, in particular in terms of lifetime, while limiting the interfering side reactions.

Thus, the present invention also relates to a process for the transformation of a feedstock comprising at least one alcohol into an olefinic effluent, said process comprising a stage of dehydration of said alcohol in which the alumina according to the invention is employed as catalyst. Advantageously, the alumina according to the invention can be employed as catalyst of the reaction for the dehydration of any type of alcohol, preferably comprising from 3 to 9 carbon atoms. The alumina according to the invention appears particularly suitable for the dehydration of secondary and tertiary alcohols, very preferably comprising from 3 to 6 carbon atoms, in order to produce the corresponding olefins.

DESCRIPTION OF THE INVENTION

The present invention relates to an alumina exhibiting a structure with a porosity such that the volume of the pores having a diameter of between 70 and 2000 Å is between 0.15 and 0.50 ml/g, and comprising at least one alkali metal (M), such that the content by weight of alkali metal, expressed as $M_2O$, is between 400 and 1500 ppm, with respect to the total weight of the alumina.

The alumina according to the invention exhibits a structure with an optimized porosity. The latter is such that the volume of the pores having a diameter of between 70 and 2000 Å (denoted $V_{70\ Å}$-$V_{2000\ Å}$) is advantageously greater than or equal to 0.15 ml/g, preferably greater than or equal to 0.20 ml/g, and less than or equal to 0.50 ml/g, preferably less than or equal to 0.40 ml/g.

The volume of the pores having a diameter of between 70 and 2000 Å, denoted $V_{70\ Å}$-$V_{2000\ Å}$, $V_{2000\ Å}$ representing the volume created by the pores with a diameter of greater than or equal to 2000 Å and $V_{70\ Å}$ representing the volume created by the pores with a diameter of greater than or equal to 70 Å, corresponds to the difference between $V_{70\ Å}$ and $V_{2000\ Å}$. It represents the volume created by all of the pores with a diameter of between 70 Å and 2000 Å. The volumes $V_{70\ Å}$ and $V_{2000\ Å}$ are measured on an alumina sample by the mercury porosimetry method according to Standard ASTM D4284-83 at a maximum pressure of 4000 bar, using a surface tension of 484 dyne/cm and a contact angle for the amorphous alumina supports of 140°.

The alumina according to the invention comprises at least one alkali metal, at an advantageously reduced content. The content by weight of alkali metals, expressed as $M_2O$, of the alumina according to the invention is in particular between 400 and 1500 ppm by weight, preferably between 400 and 950 ppm by weight, with respect to the total weight of the alumina.

Said alkali metal of the alumina according to the invention is chosen from sodium, potassium, lithium and their mixtures. The preferred alkali metal is sodium. The alkali metal is generally in its oxide form.

The alumina according to the invention thus exhibits a reduced acidity and a structure with a porosity which are optimal, in particular for the reaction for the dehydration of alcohols. The alumina according to the invention also advantageously exhibits a high isomerization capacity. In particular, the alumina according to the invention exhibits a capacity for chain isomerization of 1-butene, at 300° C., with respect to the thermodynamic equilibrium, advantageously of greater strictly than 60%. In addition, the capacity for chain isomerization of 1-butene by the alumina according to the invention, at 400° C., with respect to the thermodynamic equilibrium, is preferably greater than 80%.

Preferably, the alumina according to the invention additionally has a total pore volume (TPV) of greater than or equal to 0.50 ml/g.

According to the invention, the total pore volume TPV is determined by calculation according to the following formula:

$$TPV=1/Dg-1/Da$$

wherein (Dg) is the grain density and (Da) is the absolute density, measured by the mercury pycnometry method and the helium pycnometry method respectively.

Advantageously, the alumina exhibits a volume of the pores with a diameter of greater than or equal to 70 Å, denoted $V_{70\ Å}$, preferably of greater than or equal to 0.35 ml/g, preferentially of greater than or equal to 0.45 ml/g, in a preferred way of greater than or equal to 0.50 ml/g and more preferably still of greater than or equal to 0.52 ml/g. The volume of the pores with a diameter of greater than or equal to 70 Å, denoted $V_{70\ Å}$, is advantageously less than or equal to 0.8 ml/g, preferably less than or equal to 0.70 ml/g.

Advantageously, the alumina according to the invention exhibits a BET specific surface area of at least 65 $m^2/g$, preferably of at least 150 $m^2/g$, more preferably of at least 200 $m^2/g$. At the same time, the alumina according to the invention advantageously exhibits a BET specific surface area of at most 350 $m^2/g$, preferably of at most 325 $m^2/g$.

This specific surface area is a surface measured by the BET method, that is to say the specific surface area determined by nitrogen adsorption in accordance with Standard ASTM D 3663-78 drawn up from the Brunauer-Emmett-Teller method described in the periodical "The Journal of the American Chemical Society", 6Q, 309 (1938).

Advantageously, the alumina according to the invention contains in a preferred way at most 500 ppm by weight of silica, expressed as $SiO_2$, preferably at most 100 ppm by weight of silica, with respect to the total weight of said alumina, and more preferably is devoid of silica. Preferably, the alumina according to the invention contains in a preferred way at most 800 ppm by weight of sulphur, preferably at most 500 ppm by weight of sulphur, with respect to the total weight of said alumina. Preferably, the alumina according to the invention does not contain an active phase or additional doping agent(s) other than the elements defined above, in particular other than the alkali metal defined above.

The crystalline structure of the alumina according to the invention advantageously comprises x-alumina (chi-alumina) and amorphous alumina. The crystalline structure of the alumina according to the invention is determined by X-ray diffraction.

The alumina according to the invention preferably contains strictly less than 80% by weight of γ-alumina (gamma-alumina), preferentially strictly less than 50% by weight of γ-alumina and in a preferred way less than 35% by weight of γ-alumina. In addition, the alumina according to the invention contains advantageously strictly less than 35% by weight of q-alumina (eta-alumina), preferably strictly less than 12% by weight of q-alumina, preferentially strictly less than 8% by weight of q-alumina and more preferentially still strictly less than 5% by weight of q-alumina.

Advantageously, the alumina according to the invention can be obtained by rapid dehydration of an aluminium hydroxide or oxyhydroxide (hydrargillite, for example). Typically, the alumina according to the invention can be obtained by means of the preparation process described in Patent FR 2 527 197 by treatment in an aqueous medium having a pH of less than 9 of an active alumina powder, itself obtained by rapid dehydration of hydrargillite in a stream of hot gases, drying by atomization, then calcination according to the process described in Patent EP 0 015 196. It can also advantageously be obtained by means of the preparation process described in Patent FR 2 449 650 by treatment of an active alumina powder exhibiting a poorly crystalline and/or amorphous structure in an aqueous medium having a pH of less than 9, an alumina of poorly crystalline structure meaning an alumina such that the X-ray analysis gives a diagram exhibiting only one or a few diffuse lines corresponding to the crystal phases of low-temperature transition aluminas, that is to say essentially to the χ, ρ, η or γ phases. The alumina according to the invention can also be obtained by mixing at least two aluminas, such as, for example, the mixture of an alumina obtained according to the process described in Patent FR 2 449 650 and of an alumina obtained according to the process described in Patent FR 2 527 197.

The rapid dehydration of aluminium hydroxides or oxyhydroxides and more particularly of hydrargillite in a stream of hot gases is typically carried out in any appropriate appliance using a stream of hot gases, the inlet temperature of the gases in the appliance generally varying from 400 to 1200° C. approximately, the contact time of the hydroxide or oxyhydroxide with the hot gases generally being between a fraction of a second and 4-5 seconds. This process is described in more detail in Patent Application FR 1 108 011.

The alumina obtained by rapid calcination of aluminium hydroxides or oxyhydroxides results in an alumina having a high $Na_2O$ content, of the order of 3500 ppm. After treatment in an aqueous medium at a pH of less than 9, the $Na_2O$ content is considerably lowered. The $Na_2O$ content, after treatment in an aqueous medium at a pH of less than 9, is generally less than or equal to 2000 ppm by weight, typically less than or equal to 1500 ppm by weight. Advantageously, after treatment in an aqueous medium at a pH of less than 9, the $Na_2O$ content of the alumina according to the invention is between 400 and 1500 ppm by weight, preferably between 400 and 950 ppm by weight.

The alumina according to the invention can advantageously be provided in all the known normal forms, such as in the form of a powder, beads, extruded and crushed materials. The beads and the extrudates will be preferred. The size of the beads will then usefully be between 0.5 and 10 mm, preferably between 0.7 and 8 mm and preferentially between 0.8 and 5 mm. The extrudates can be of cylindrical or polylobate form, and be solid or hollow; their size will usefully be between 0.5 and 5 mm, preferably between 0.7 and 3 mm.

In one embodiment, the alumina prepared can be granulated, that is to say formed, preferably in the form of beads. The beads are subsequently preferably matured at a temperature of between 80 and 130° C. The matured beads are finally calcined at a temperature of between 400 and 1100° C.

By way of example, the beads can be obtained by means of a rotating technology, by agglomeration of an alumina powder in a granulator or a drum. In a known way, this type of process makes it possible to obtain beads with a diameter and with pore distributions which are controlled, these dimensions and these distributions generally being created during the agglomeration stage. The porosity can be created by different means, such as the choice of the particle size distribution of the alumina powder or the agglomeration of several alumina powders with different particle size distributions. Another method consists in mixing, with the alumina powder, before or during the agglomeration stage, a compound, known as porogenic compound, which disappears by heating and which thus creates a porosity in the beads. Mention may be made, as porogenic compound used, by way of example, of wood flour, charcoal, sulfur, tars, plastics or emulsions of plastics, such as polyvinyl chloride, polyvinyl alcohols, naphthalene or the like. The amount of porogenic compounds added is determined by the volume desired. One or more heat treatments will then complete the forming of the beads.

In another embodiment, the alumina prepared can be in the form of extrudates, for example obtained by kneading and then extruding an alumina gel, or an alumina powder, or a mixture of different starting materials.

The present invention also relates to a process for the transformation of a feedstock comprising at least one alcohol into an olefinic effluent, said process comprising a stage of dehydration of said alcohol in the presence of the alumina according to the invention.

Advantageously, the alumina according to the invention makes it possible to achieve a high conversion rate of the alcohol, in particular of secondary and/or tertiary alcohol, into olefin, in particular of greater than or equal to 30%, preferably of greater than or equal to 50%, preferentially of greater than or equal to 65% and more preferably still of greater than or equal to 70%.

According to the invention, olefinic effluent means an effluent comprising more than 25% by weight of olefins, preferably more than 50% by weight of olefins, preferentially at least 60% by weight of olefins, more preferentially at least 75% by weight of olefins and more preferably still at least 90% by weight of olefins, with respect to the weight of said effluent, preferably of corresponding (or targeted) olefins, that is to say olefins having the same number of carbon atoms as the alcohol included in the feedstock.

The feedstock to be treated advantageously comprises at least one alcohol, in particular at least 50% by weight of alcohol, preferably at least 70% by weight, preferentially at least 80% by weight, more preferably at least 85% by weight and more preferably still at least 90% by weight of said alcohol, with respect to the weight of said feedstock. The feedstock can comprise an alcohol or a mixture of alcohols. The alcohols of the feedstock can be produced from petroleum products or from chemical products or else can originate from biomass.

The alumina according to the invention is used as catalyst for the dehydration of any type of alcohol in order to produce the corresponding olefin, that is to say the olefin having the same number of carbon atoms. The alcohols having from 3 to 9 carbon atoms, preferably from 4 to 6 carbon atoms, in particular 4 carbon atoms, are preferred.

The alumina according to the invention is advantageously used as catalyst for the dehydration of secondary and/or tertiary alcohols, in particular of tertiary alcohols. According to one embodiment of the invention, the feedstock comprises a secondary alcohol chosen from: isopropanol, 2-butanol, 3-methylbutan-2-ol, pentan-2-ol, pentan-3-ol and their mixtures. According to another embodiment of the invention, the feedstock comprises a tertiary alcohol chosen from: 2-methylpropan-2-ol (tert-butanol or tert-butyl alcohol or tertiary butyl alcohol, denoted TBA) and/or 2-methylbutan-2-ol (tertiary pentanol or tert-amyl alcohol, denoted TAA). Preferably, the alumina according to the invention is used to catalyse the dehydration of 2-methylpropan-2-ol (tert-butanol) to give isobutene and/or the dehydration of 2-methylbutan-2-ol (or tert-pentanol) to give 2-methylbut-2-ene and/or 2-methylbut-1-ene.

The dehydration stage comprises a reaction section comprising one or more reactors comprising the catalyst. The reactor(s) can be (a) noncontinuous reactor(s) or (a) continuous fixed bed reactor(s) (radial, isothermal, adiabatic, and the like). In a preferred form, the dehydration takes place continuously in a fixed bed reactor configuration using several reactors in series of equal or different sizes and/or several "permutable" reactors operated in parallel. Advantageously, the dehydration reaction is carried out in at least two separate reactors, preferably between 2 and 6 separate reactors, in particular in 4 separate reactors, preferably in series, it being possible for the effluent obtained at the outlet of a reactor to advantageously be reheated before being sent to the following reactor.

The dehydration reaction is carried out, in the reaction section, under conditions known to a person skilled in the art, typically in the gas phase, in the liquid phase or in a mixed phase (that is to say, a mixture of gas and liquid phases), preferably in the gas phase, at a temperature of between 200° C. and 450° C., preferably between 225° C. and 410° C., at a pressure of between 0.1 and 4 MPa, preferably between 0.5 and 2 MPa, and with an hourly space velocity (HSV) of between 0.5 $h^{-1}$ and 10 $h^{-1}$, preferably between 2 $h^{-1}$ and 7 $h^{-1}$.

Hourly space velocity (HSV) means the ratio of the flow rate by volume of the feedstock at the reactor inlet in $m^3$/h at 15° C., 1 atm, divided by the volume of catalyst in $m^3$ present in the reactor.

According to a preferred embodiment of the invention, the process is a process for the transformation of a feedstock comprising at least one secondary alcohol, one tertiary alcohol or their mixture into an olefinic effluent, said process comprising a stage of dehydration of said alcohol which comprises a reaction section carried out in the presence of the alumina according to the invention, in the gas phase, in the liquid phase or in a mixed phase, preferably in the gas phase, at a temperature of between 200° C. and 450° C., at a pressure between 0.1 and 4 MPa and with an hourly space velocity (HSV) between 0.5 $h^{-1}$ and 10 $h^{-1}$. The absolute pressure at the reaction section inlet is advantageously chosen such that the feedstock is in the gas phase at the inlet of the reactor.

According to a very particular embodiment of the invention, the process is a process for the transformation of a feedstock comprising at least one secondary alcohol advantageously comprising 4 carbon atoms into an olefinic effluent, said process comprising a stage of dehydration of said alcohol which comprises a reaction section carried out in the presence of the alumina according to the invention, preferably in the gas phase, at a temperature of between 350° C. and 450° C., more preferably of between 350° C. and 400° C., at a pressure preferably of between 0.5 and 1.2 MPa and with an hourly space velocity (HSV) of between 2 $h^{-1}$ and 7 $h^{-1}$. The absolute pressure at the reaction section inlet is advantageously chosen such that the feedstock is in the gas phase at the inlet of the reactor.

According to another very particular embodiment of the invention, the process is a process for the transformation of a feedstock comprising at least one tertiary alcohol advantageously comprising 4 carbon atoms into an olefinic effluent, said process comprising a stage of dehydration of said alcohol which comprises a reaction section carried out in the presence of the alumina according to the invention, preferably in the gas phase, at a temperature of between 250° C. and 410° C., more preferably of between 275° C. and 380° C., at a pressure preferably of between 0.5 and 1.7 MPa and with an hourly space velocity (HSV) of between 2 $h^{-1}$ and 4 $h^{-1}$. The absolute pressure at the reaction section inlet is advantageously chosen such that the feedstock is in the gas phase at the inlet of the reactor.

Advantageously, the alumina used as catalyst in the present invention can be regenerated, in particular several times, for example by carrying out the controlled incineration of the coke deposited on the alumina during the reaction. Thus, the transformation process according to the invention can advantageously be carried out continuously in several parallel "permutable" reactors; when one or more reactors operate(s), another undergoes a regeneration of the catalyst.

The process according to the invention can optionally comprise a stage of purification of the feedstock, upstream of the dehydration stage comprising the reaction section. This optional purification stage, comprising at least one purification section, makes it possible to remove the impurities, for example the organic impurities, possibly nitrogen-comprising or sulphur-comprising organic impurities, capable of affecting the catalyst of said reaction section. Any purification method known to a person skilled in the art can be used in said purification section(s).

Advantageously, the process according to the invention can typically comprise, in addition, one or more other sections, such as a heating section, for heating the feedstock to be treated before it enters the reaction section, a separation section, in order to separate the effluent at the reaction section outlet and to recover the different products obtained, or a purification section, in order to recover a purified olefinic effluent, in particular comprising at least 90% by weight of targeted olefins.

The alumina according to the invention can also be used as adsorbent.

A better understanding of the invention will be obtained in the light of the following examples, presented by way of illustration and without limitation.

Measurement Methods

Mercury Porosimetry Method

The volume of the pores with a diameter of greater than or equal to 70 Å ($V_{70\ Å}$) and the volume of the pores with a diameter of greater than or equal to 2000 Å($V_{2000\ Å}$) are measured on an alumina sample by the mercury porosimetry method according to Standard ASTM D4284-83 at a maximum pressure of 4000 bar, using a surface tension of 484 dyne/cm and a contact angle for the amorphous alumina supports of 140°.

Kelvin's law gives the relationship between the pressure, the diameter of the smallest pore into which the mercury penetrates at said pressure, the wetting angle and the surface tension according to the formula: $Ø=(-4\gamma \cos \theta)/P$ in which:

Ø represents the diameter of the pore,

γ represents the surface tension of the mercury,

θ represents the contact angle between the mercury and the solid,

P represents the absolute pressure.

In practice, the alumina sample is placed in a column, into which mercury is introduced under a pressure P. As the mercury does not wet the alumina, its penetration or its non-penetration into the pores of the sample having a given diameter is a function of the value of P. The finest pores require, in order to be filled, the establishment of a higher pressure P than for the filling of the coarser pores. The measurement of the amount of mercury penetrating into the sample for different values of P makes it possible to determine the volume occupied by the pores with a diameter greater than given values of this diameter.

Measurement of the Capacities for Chain Isomerization of 1-Butene 500 mg of alumina according to the invention that is ground (size of the particles of between 400 and 500 μm) are introduced into a glass reactor. The product is conditioned in situ at 300° C. for 2 h under helium flow at a flow rate of 3.9 l/h. The temperature of the reactor is subsequently increased while passing through two stationary phases at 300° C. and then 400° C. At each stationary temperature phase, three injections of 0.2 ml of butene into the reactor are carried out, the reactor always being maintained under helium flow at 3.9 l/h.

The outlet gases are analysed by gas chromatography. The analysis makes it possible to measure the amount of unconverted 1-butene and also the amount of cis-2- and trans-2-butene formed.

The theoretical thermodynamic equilibrium constant Kth (T) is determined by calculation and the true equivalent constant K(T) is determined by the result of the measurements.

$$Kth(T) = \frac{[\text{cis-2-butene}]e + [\text{trans-2-butene}]e}{[\text{1-butene}]e + [\text{cis-2-butene}]e + [\text{trans-2-butene}]e}$$

$$K(T) = \frac{[\text{cis-2-butene}] + [\text{trans-2-butene}]}{[\text{1-butene}] + [\text{cis-2-butene}] + [\text{trans-2-butene}]}$$

in which T is the temperature of the butene at the outlet of the reactor. The other values represent the concentrations at the reactor outlet or at equilibrium ([ ]e) for said temperature T. The isomerizing power or isomerization rate A(T) is given by the following formula:

$$A(T) = \frac{K(T) \times 100}{Kth(T)}$$

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. FR 1856905, filed Jul. 25, 2018 are incorporated by reference herein.

EXAMPLES

Example 1

Each of the aluminas A to I (cf. Table 1) is prepared in the following way:

Hydrargillite powder is subjected to a rapid dehydration at 1000° C., using a stream of hot gas, in order to obtain a powder 1 containing 3200 ppm by weight of $Na_2O$. A part of the powder 1 is treated in an aqueous medium in order to give a powder 2, the $Na_2O$ content of which is 500 ppm by weight. The powders 1 and 2 are mixed. The mixture is subsequently granulated in the form of beads with water, optionally in the presence of a porogenic compound, in order to obtain an alumina in the bead form exhibiting a sodium content dependent on the powder 1 to powder 2 ratio.

The beads are matured and then calcined.

The characteristics of the aluminas A to I prepared are given in Table 1. Furthermore, the aluminas A to I obtained contain less than 500 ppm by weight of silica.

Example 2

The capacities for isomerization of 1-butene are determined for each of the aluminas A to I prepared according to Example 1, in accordance with the method and the operating conditions described above.

The results are given in Table 1. They correspond to the mean of the three injections of butene carried out at 300° C. and to the mean of the three injections carried out at 400° C.

TABLE 1

| Alumina | $Na_2O$ content ppm by weight | $V_{70\,Å}$ ml/g | $V_{2000\,Å}$ ml/g | $V_{70\,Å} - V_{2000\,Å}$ ml/g | Specific surface area SBET $m^2/g$ | Total pore volume (TPV) ml/g | isomerization Rate at (T) (T = 300° C.) % | (T = 400° C.) % |
|---|---|---|---|---|---|---|---|---|
| A | 700 | 0.398 | 0.128 | 0.270 | 270 | 0.537 | 93.3 | 94.8 |
| B | 700 | 0.557 | 0.207 | 0.350 | 260 | 0.655 | 92.5 | 94.0 |
| C | 500 | 0.548 | 0.187 | 0.361 | 260 | 0.585 | 92.7 | 94.2 |
| D | 500 | 0.625 | 0.170 | 0.455 | 180 | 0.680 | 46.3 | 92.2 |
| E | 2000 | 0.333 | 0.180 | 0.153 | 360 | 0.555 | 9.0 | 55.6 |
| F | 2000 | 0.169 | 0.039 | 0.130 | 350 | 0.445 | 19.6 | 70.6 |
| G | 3200 | 0.234 | 0.053 | 0.181 | 335 | 0.441 | 1.7 | 26.6 |
| H | 500 | 0.744 | 0.047 | 0.697 | 105 | 0.752 | 9.5 | 57.3 |
| I | 500 | 0.534 | 0.410 | 0.124 | 7 | 0.535 | 0.5 | 7.6 |

The isomerization capacity of the aluminas A to D according to the invention is greater than that of the aluminas E to I not in accordance with the invention.

Example 3

Tests on the dehydration of isopropanol in the presence of the aluminas A to I in pilot scale reactors.

Each of the aluminas A to I is tested in the following way:

An alumina sample is ground in order to obtain a powder with a particle size distribution between 0.8 and 1 mm. A pilot reactor is filled with 0.4 g of ground alumina. In the reactor, the ground alumina is heated at 400° C. for 2 hours. After returning to the temperature of the experiment (T=225° C.), the alumina sample is subjected to twelve consecutive injections of a stream consisting of nitrogen which has passed through an isopropanol bath maintained at 30° C., with a flow rate of 4 l/h. The entering and exiting streams of each of the injections are analysed by gas chromatography.

The results given in Table 2 correspond to the measurement carried out after the twelfth injection.

It is apparent that the main product of the reaction is propylene, corresponding to the product of the dehydration reaction of isopropanol. The chromatographic analyses also show that diisopropyl ether, the product of the secondary condensation reaction, and acetone, the product of the secondary dehydrogenation reaction, are in small amounts

TABLE 2

Conversion of isopropanol and selectively for propylene obtained at 225° C. in the presence of the aluminas A to I

| | | A | B | C | D | E | F | G | H | I |
|---|---|---|---|---|---|---|---|---|---|---|
| Isopropanol conversion | % | 67 | 73 | 72 | 30 | 12 | 21 | 3 | 9 | <1 |
| Selectivity for propylene | % | 97 | 98 | 98 | 75 | ns | 50 | ns | ns | ns |

ns = not significant

In the presence of the aluminas A to D according to the invention, the degrees of conversion are highly satisfactory and the selectivities for propylene are high. The catalytic performances obtained for the aluminas A to D in accordance with the invention obtained during the dehydration reaction of an alcohol, such as isopropanol, are better than those obtained with the aluminas E to I not in accordance.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. An alumina exhibiting a structure with a porosity such that the content of pores having a diameter of between 70 and 2000 Å is between 0.15 and 0.50 ml/g, and comprising at least one alkali metal (M), such that the content by weight of alkali metal, expressed as $M_2O$, is between 400 and 1500 ppm, with respect to the total weight of the alumina, wherein the alumina exhibits a BET specific surface area of at least 150 $m^2/g$ and wherein the alumina contains at most 500 ppm by weight of silica, expressed as $SiO_2$.

2. The alumina according to claim 1, in which the volume of the pores having a diameter of between 70 and 2000 Å is greater than or equal to 0.20 ml/g, and less than or equal to 0.40 ml/g.

3. The alumina according to claim 1, in which the content by weight of alkali metal, expressed as $M_2O$, is between 400 and 950 ppm, with respect to the total weight of the alumina.

4. The alumina according to claim 1, in which the total pore volume is greater than or equal to 0.50 ml/g.

5. The alumina according to claim 1, exhibiting a volume of the pores with a diameter of greater than or equal to 70 Å, denoted $V_{70\ Å}$, of greater than or equal to 0.35 ml/g.

6. The alumina according to claim 1, exhibiting a BET specific surface area of at least 200 $m^2/g$, and of at most 350 $m^2/g$.

7. The alumina according to claim 1, containing at most 100 ppm by weight of silica, expressed as $SiO_2$.

8. The alumina according to claim 1, having a structure comprising χ-alumina and amorphous alumina.

9. The alumina according to claim 1, containing strictly less than 80% by weight of γ-alumina.

10. The alumina according claim 1, containing strictly less than 35% by weight of η-alumina.

11. The alumina according to claim 1, obtained by rapid dehydration of an aluminium hydroxide or oxyhydroxide.

12. A process for the transformation of a feedstock comprising at least one alcohol into an olefinic effluent, said process comprising a stage of dehydration of said alcohol in the presence of the alumina according to claim 1.

13. The process according to claim 12, in which the feedstock comprises at least 50% by weight of alcohol, with respect to the weight of said feedstock.

14. The process according to claim 12, in which said alcohol comprises from 3 to 9 carbon atoms.

15. The process according to claim 12, in which said alcohol is a secondary and/or tertiary alcohol.

16. The process according to claim 12, in which the dehydration stage comprises a reaction section in which the dehydration reaction is carried out in the gas phase, in the liquid phase or in a mixed phase, at a temperature of between 200° C. and 450° C., at a pressure of between 0.1 and 4 MPa and with an hourly space velocity (HSV) of between 0.5 $h^{-1}$ and 10 $h^{-1}$.

* * * * *